United States Patent [19]

Wedel

[11] Patent Number: 4,497,325
[45] Date of Patent: Feb. 5, 1985

[54] ULTRASOUND NEEDLE, BIOPSY INSTRUMENT OR CATHETER GUIDE

[76] Inventor: Victor J. Wedel, P.O. Box 182, Kalona, Iowa 52247

[21] Appl. No.: 398,623

[22] Filed: Jul. 15, 1982

[51] Int. Cl.³ ............................................ A61D 10/00
[52] U.S. Cl. ................................. 128/754; 408/115 R; 83/829; 604/116
[58] Field of Search ................. 128/24 A, 303 B, 660, 128/735, 754; 604/116–117; 408/115 R; 83/521, 699, 829

[56] References Cited

U.S. PATENT DOCUMENTS

| | | | |
|---|---|---|---|
| 1,072,328 | 9/1913 | Goodrich | 408/115 |
| 1,372,378 | 3/1921 | Walker | 408/115 |
| 2,451,183 | 10/1948 | Tantimonaco | 128/303 B |
| 2,536,963 | 1/1951 | Stephens | 408/115 |
| 3,017,887 | 1/1962 | Heyer | 604/116 |
| 3,556,079 | 1/1971 | Omizo | 128/661 |
| 3,721,337 | 3/1973 | Larson et al. | 206/150 |
| 4,029,084 | 6/1977 | Soldner | 128/660 |
| 4,058,114 | 11/1977 | Soldner | 128/660 |
| 4,108,165 | 8/1978 | Kopp et al. | 128/660 |
| 4,132,496 | 1/1979 | Casto | 408/115 R |
| 4,249,539 | 2/1981 | Vilkomerson et al. | 128/660 |
| 4,289,139 | 9/1981 | Enjoji | 128/660 |
| 4,332,248 | 6/1982 | DeVitis | 604/117 |
| 4,363,326 | 12/1982 | Kopel | 128/24 A |
| 4,402,324 | 9/1983 | Lindgren et al. | 128/660 |

Primary Examiner—William E. Kamm
Assistant Examiner—Mitchell J. Shein
Attorney, Agent, or Firm—James C. Nemmers

[57] ABSTRACT

An attachment for use in connection with ultrasound transducers to assist in conducting various surgical procedures involving the withdrawal of fluid from or injection of fluid into selected body organs or biopsies of various organs. The attachment serves to accurately guide a needle or catheter into the selected site scanned by the ultrasound transducer. The device employs a removable and rotatable guide that provides for the use of instruments of different sizes for insertion in body parts within a wide range of angles.

7 Claims, 4 Drawing Figures

ULTRASOUND NEEDLE, BIOPSY INSTRUMENT OR CATHETER GUIDE

BACKGROUND OF THE INVENTION

The invention relates to an attachment used in connection with ultrasound transducers for certain surgical procedures in which a needle, biopsy instrument or catheter is inserted into an internal organ of the patient.

Diagnostic ultrasound equipment uses sound waves of a very high frequency directed into the body via a piezoelectric crystal transducer. As the sound waves penetrate the body, they will be reflected back to the transducer from various organs. These returning "echos" produce a cross-sectional image of the human body being scanned. Initially, almost all ultrasound practices had been conducted with static imaging systems which produce a single, static image. Use of static scanners was preferred over "real-time" scanners because of the higher quality of the image produced by the static scanner. However, because of advances in electronic technology, the image quality of the real-time scanner is now comparable to that of the best static scanner, and thus real-time scanners are being used with increasing frequency. These real-time scanners present two dimensional information as it happens because the tissue being examined is rapidly and repeatedly scanned producing information that is displayed on a conventional cathode-ray tube or screen. The observer therefore summates many images each second and sees them as a continuous image on the screen. There are various types of real-time scanners, and the sector-type scanner provides an image over a wider range than the linear-type scanners.

With these improved ultrasound scanners, diagnostic procedures are becoming available to explore and evaluate almost any part of the human anatomy. Diagnostic ultrasound is becoming the exclusive technique for obstetrical imaging because it does not involve any radiation danger to the mother or the growing fetus. For this reason, amniocentesis is becoming increasingly used as a diagnostic aid by obstetricians. However, because of the dynamics of both the uterus and the fetus, it is imperative that amniocentesis be performed at the same time as sonography, and even so, it is possible to accidentally strike the fetus with the needle during the procedure. This is true notwithstanding good visual control in the scanning region, since up to the time the needle enters the scanned area, the puncturing sequence must be carried out blindly. If penetration is not correct, the needle or cannula must be withdrawn and reinserted causing additional invasive trauma to the patient.

To improve the accuracy of penetration, there have been designed various devices for assisting in guiding the needle, cannula or catheter into the selected body site. Many of these guides are fixed and the angle of penetration is somewhat indirect thus detracting from the accuracy of penetrating the ultimate target site within the body of the patient. Tolerances are very close particularly when the site involves a dynamic organ and a moving fetus. Moreover, some of these devices require the use of a cannula, which increases the trauma to the patient, and because of its relatively large size, requires greater accuracy of penetration. There is therefore a need for an improved guide which will improve the precision of penetration to the ultimate target site within the body of the patient. There is also a need for a device which will allow easy adjustability of the angle of penetration and permit the needle to move once penetration has occurred if the target site moves. There is a further need for a device which will allow the needle or catheter to remain in place in the body part while allowing easy removal of the transducer and guide. There is a further need for a simple and inexpensive device that can be easily accommodated to needles and catheters of various sizes.

SUMMARY OF THE INVENTION

The device of the invention is preferably used in connection with sector-type ultrasound transducers, and it is designed to be attached to the transducer in a quick and easy manner so as to provide a more direct angle of penetration into the body part being scanned. The device includes a removable needle guide that is mounted for rotation within a selected range, thus providing for varying the angle of penetration, and once penetration has occurred, if the body part moves, the needle will move minimizing the possibility of laceration of the tissue. The guide portion of the device of the invention also allows for the use of a needle or catheter of any selected size, and because the guide portion is easily separable from the device, both the guide and the entire device, although with the ultrasound transducer, can be quickly and easily separated from the needle or catheter leaving it in the body part.

The device of the invention not only greatly improves the precision of the various procedures for which the device is designed, but the device is extremely simple, can be adapted to fit transducers of various manufacturers, and can be produced and marketed at a reasonable cost.

DETAILED DESCRIPTION OF THE PREFERRED EMBODIMENTS OF THE INVENTION

Figure 1:
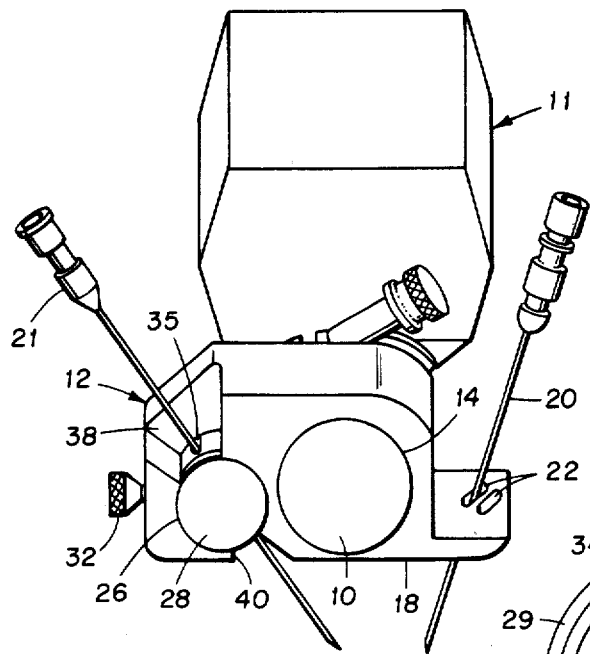
FIG. 1 is a perspective view of the device of the invention shown mounted on an ultrasound transducer and with needles shown in place.
Figure 2:
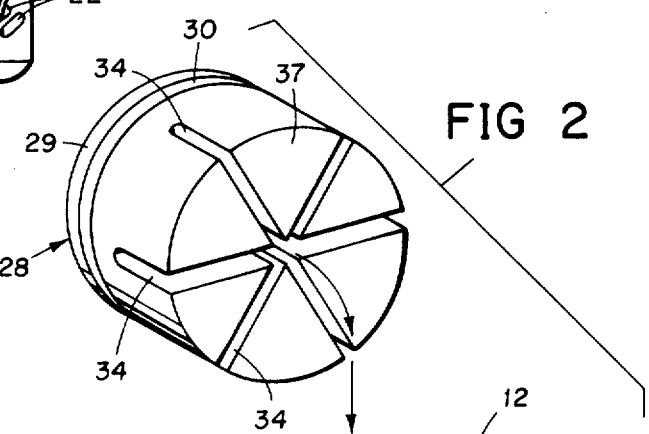
FIG. 2 is an exploded perspective view of that portion of the device where the removable guide is located.

In the drawings, I have illustrated a transducer 10 of an ultrasound real-time scanner 11 of the sector-type. The tranducer 10 is normally placed on the area of the patient above the body part that is to be scanned. The device of the invention includes a main body 12 which has a mounting opening 14 that is of a size to exactly accommodate the transducer 10. The size, shape and angle of the transducer 10 varies from manufacturer to manufacturer, and thus the exact shape and location of the mounting opening 14 in the main body 12 will depend upon the particular transducer with which the device of the invention is to be used. Obviously, it is within the skill of those in the art to modify the main body 12 to accommodate transducers of the various manufacturers.

In any event, the main body 12 will also be provided with an opening 16 in the contact surface 18 near the mounting opening 14 so that when the device of the invention is in place on the transducer 10, the transducer can contact the skin of the patient in the area to be scanned. Also, if desired or necessary, a thumb screw or other suitable device (not shown) can be used to positively secure the device to the transducer 10.

On one side of the mounting opening 14, the main body 12 also includes fixed guide openings 22 which are formed close to the mounting opening 14 and at the proper place in the main body 12 so that when the medical instrument such as needle 20 is inserted through one of the openings 22 it will be in the plane of the scan of transducer 10 and also at an appropriate acute angle allowing for the most direct penetration into the desired body part of the patient.

On the side of the main body 12 opposite to the mounting opening 14, there is formed a circular opening 26 the axis of which is perpendicular to the plane of the scanner. Circular opening 26 is also formed in close proximity to the mounting opening 14. Removably received in the circular opening 26 is a cylindrical shaped guide member 28 which has a shoulder 29 and a circumferential groove 30 for receiving the end of a thumb screw 32 when the guide member 28 is properly in place in the circular opening 26. The thumb screw 32, when tightened, serves to prevent axial movement of the guide member 28 within circular opening 26 while still permitting the circular guide to freely rotate. Of course, any other suitable locking device, such as a spring-loaded pin, could be used in place of thumb screw 32 as long as the locking device permits quick and easy removable of the guide member 28 from the main body 12.

The guide member 28 has formed in it a plurality of guide grooves 34 each of which extends along a diameter of the guide member 28 and through surface 37 of the guide member 28. Each groove 34 may be of a different width so as to accommodate a medical instrument, such as a needle or catheter, of a different diameter. The depth of the guide grooves 34 are such that when the guide member 28 is properly positioned within the opening 26 and locked by thumb screw 32 from axial movement, groove 34 will present a guide opening 35 (FIG. 1) that is just slightly larger than the diameter of the selected medical instrument. Also, the guide openings 35 thus formed is in the exact plane of the scanner. Thus, a medical instrument such as needle 21 inserted through the guide opening 35 thus formed by the properly positioned guide member 28 can be easily advanced through the guide opening 35 but movement of the needle within opening 35 will be restricted within the narrow plane of the scanner.

To provide for insertion of the needle 21 through the device of the invention when the guide member 28 is properly positioned in opening 26, there is formed in the main body 12 above the opening 26 a segmental-shaped opening 38. Similarly, there is a segmental-shaped opening formed in main body 12 extending from the circular opening 26 through the contact surface 18 of the main body 12. The width of segmental-shaped openings 38 and 40 are such so as to provide for a wide range of movement of needle 21 when it is properly inserted through guide opening 35 in the guide member 28. This is best illustrated in FIG. 1. However, since the guide member 28 is free to rotate within opening 26, a needle that has penetrated into the body tissue and into a dynamic body organ is free to move within the plane of the scan in the event that the body part moves. This greatly minimizes the possibility of laceration of the tissue.

Because the guide member 28 is removable quickly and easily, it allows different guide members having different size guide grooves 34 to be used depending upon the particular surgical procedure to be conducted. For example, if a catheter is to be inserted into an internal body organ, a guide member 28 having guide grooves 34 of sufficient width to accommodate a catheter can be used. Also, since the guide member 28 is easily removable and separable from the main body 12, and since the guide grooves 34 extend through surface 37 of the member 28, this provides for removal of the entire device while leaving the catheter or needle in place in the body part. In other words, once penetration of the needle or catheter into the body part has occurred, the thumb screw 32 can be loosened permitting the main body 12 and transducer 10 to be separated from the guide member 28. After this separation occurs, the guide member 28 can be then easily separated from the needle or catheter.

Figure 3:
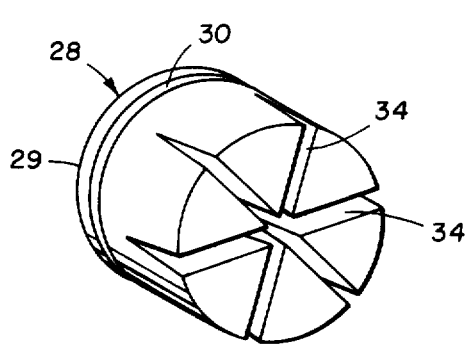
FIG. 3 is a perspective view of a different embodiment of the removable guide.

If desired, the guide grooves 34 may be slightly tapered outwardly toward surface 37 of guide member 28 so as to facilitate easy separation of the guide member 28 from the needle or catheter. This is illustrated in the embodiment of FIG. 3.

Figure 4:
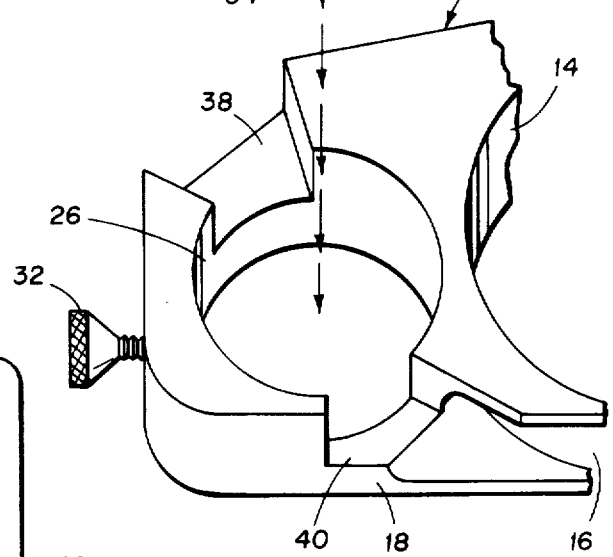
FIG. 4 is an illustration of the screen of the scanner and showing a guide template positioned to assist in surgical procedures using the device of the invention.
Figure 4:
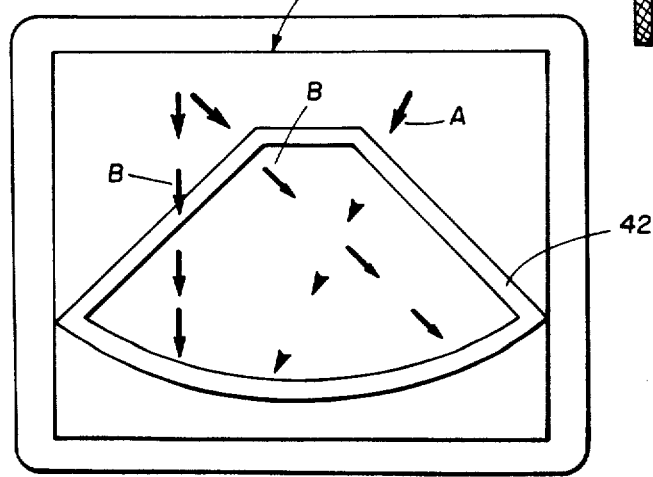

In FIG. 4, I have illustrated a viewing screen 42 over which a template 43 is placed to further insure accuracy of penetration. This will be illustrated in the following brief description of the procedure for using the device of the invention.

Preferably, the transducer 10 is used to scan a patient until the portion of the body part to be penetrated is located on the viewing screen 42. The position of the scanner at this point can then be marked on the patient and the area properly cleaned and sterilized. The device of the invention is then mounted on the transducer 10, and the transducer 10 with the device in place is positioned on the previously marked skin area. Precise position of the transducer 10 can be aided by use of the template 43 (FIG. 4) in which the line of arrows "A" represents the fixed guide openings 22 and the two lines of arrows "B" represent the variable angle provided by the guide member 28. A guide member 28 is then selected containing the proper size guide grooves 34, and the member 28 is inserted in the circular opening 26 and the thumb screw 32 tightened to prevent further axial movement of the guide member 28. The needle 21, catheter or other surgical instrument is then inserted into the guide opening formed by guide groove 34 along an angle between the lines of arrows "B" on the template 43. This angle of insertion is in the angular range defined by the segmental openings 38 and 40. Progress of the needle 21 is, of course, carefully watched on the viewing screen 42, and if for any reason the body part has moved or the angle of insertion has varied slightly from the target provided by the lines of arrows "B" on the template, the needle 21 can be withdrawn and reinserted. However, this is unlikely if the procedure is properly and carefully followed.

Because of the design and close proximity of the guide member 28 to the transducer 10, the angle of penetration of needle 21 will be an acute angle and more direct than that provided by prior art devices which provide for an angle of insertion approaching in some instances an angle of penetration in excess of 45°. This greatly improves the accuracy and minimizes the possibility of penetrating the organ at the wrong site. This is especially important in procedures such as amniocentisis where a moving fetus might be accidentally struck with a needle.

The device of the invention also allows for quick and easy change of the guide member 28 so as to accommodate needles and catheters of various sizes depending upon the particular procedure to be conducted. This can be done without sacrifice of any precision and can be quickly and easily done during a single procedure if for any reason the surgeon must change the needle or catheter during the procedure. This can also be done without moving the transducer 10. Also, as previoulsy described, if it is desired to leave the needle or catheter in place, this can be quickly and easily accomplished by loosening the set screw 32, separating the guide 28 from the main body 12, and then easily separating the guide 28 from the needle.

Also, the device of the invention eliminates the necessity of using cannulas which are required by some prior art devices such as that shown in U.S. Pat. No. 4,058,114. The elimination of the use of a cannula reduces the invasive trauma to the patient and also reduces the likelihood of causing damage to internal organs, and in procedures such as amniocentisis minimizes the risk of aborting the fetus.

Having thus described the invention in connection with a preferred embodiment thereof, it will be obvious to those skilled in the art that various revisions and modifications can be made to the preferred embodiment without departing from the spirit and scope of the invention. It will be further obvious to those skilled in the art that the device may have uses in various surgical procedures not yet attempted because of the risk involved. Such uses may be adopted in the future because of the precision and accuracy provided for by use of the device of the invention. It is my intention however that all such revisions and modifications to the preferred embodiment that are obvious to those skilled in the art, as well as its use in connection with all types of medical procedures, will be included within the scope of the following claims.

What is claimed is:

1. A device for use in connection with an ultrasound transducer for guiding medical instruments through the skin and into a selected body part of a patient, said device comprising a main body, attachment means on said main body providing for operative connection of the device to a transducer, said main body having a contact surface for engaging the skin of the patient in the area of the selected body part, said main body also having a cylindrical-shaped opening with the axis of the opening parallel to the plane of the contact surface, and a cylindrical-shaped guide member removably positioned in said cylindrical-shaped opening and turnable about said axis, said cylindrical-shaped guide member having a plurality of guide slots formed therein each along a diameter of said guide member to receive a medical instrument therein.

2. The device of claim 1 in which said guide slots are of different widths.

3. The device of claim 2 in which the guide slot in the cylindrical-shaped guide member are tapered with each slot being of the same width along a selected diameter but tapered so as to be wider at one end of said guide member.

4. The device of claim 1 in which said cylindrical-shaped guide member is positioned near the attachment means of said main body so that said guide slot provides for insertion of a medical instrument at a direct angle of penetration.

5. The device of claim 1 in which there is included locking means for holding said cylindrical-shaped suide member in a selected position relative to the main body member while providing for easy separation of said cylindrical-shaped guide member from the main body when said locking means is unlocked.

6. The device of claim 5 in which the guide slot in said cylindrical-shaped guide member extends through the surface at one end of said guide member thereby providing for separation of the cylindrical-shaped guide member from the main body without disturbing a medical instrument that has been inserted through the guide slot.

7. The device of claim 1 in which the main body also has a fixed guide opening extending through the contact surface at a point close to the attachment means.

* * * * *